United States Patent [19]

Banks

[11] 4,432,853
[45] Feb. 21, 1984

[54] METHOD OF MAKING AN ION BEAM SPUTTER-ETCHED VENTRICULAR CATHETER FOR HYDROCEPHALUS SHUNT

[75] Inventor: Bruce A. Banks, Olmsted Township, Cuyahoga County, Ohio

[73] Assignee: The United States of America as represented by the Administrator of the National Aeronautics and Space Administration, Washington, D.C.

[21] Appl. No.: 444,124

[22] Filed: Nov. 24, 1982

Related U.S. Application Data

[62] Division of Ser. No. 272,407, Jun. 10, 1981, Pat. No. 4,377,169.

[51] Int. Cl.³ ............................................. A61B 27/00
[52] U.S. Cl. ................................ 204/192 E; 156/643; 156/644; 156/668
[58] Field of Search .................... 204/192 E; 156/643, 156/644, 668; 604/8, 280

[56] References Cited

U.S. PATENT DOCUMENTS

| | | | |
|---|---|---|---|
| 3,410,979 | 11/1968 | Larsson | 219/68 |
| 3,437,088 | 4/1969 | Bielinski | 128/348 |
| 3,595,241 | 7/1971 | Sheridan | 128/350 |
| 3,633,585 | 1/1972 | McDonald, Jr. | 128/348 |
| 3,656,988 | 4/1972 | Steffen et al. | 117/5.5 |
| 3,753,439 | 8/1973 | Brugarolas et al. | 128/350 R |
| 3,823,720 | 7/1974 | Tribble | 128/350 R |
| 4,038,513 | 7/1977 | Steigerwald | 219/121 EM |
| 4,072,153 | 2/1978 | Swartz | 128/350 R |
| 4,083,369 | 4/1978 | Sinnreich | 128/276 |
| 4,121,595 | 10/1978 | Heitmann | 131/21 R |
| 4,182,343 | 1/1980 | Inaba | 128/350 R |
| 4,280,500 | 7/1981 | Ono | 128/348 |

FOREIGN PATENT DOCUMENTS

2233028 6/1973 France ............................ 128/350 R

OTHER PUBLICATIONS

P. D. Townsend et al., *Ion Implantation, Sputtering and Their Applications*, Academic Press, London, 1976, pp. 247-261.
J. L. Vossen et al., *Thin Film Processes*, Academic Press, New York, 1978, pp. 497-556.

*Primary Examiner*—G. L. Kaplan
*Assistant Examiner*—William Leader
*Attorney, Agent, or Firm*—Norman T. Musial; John R. Manning; Gene E. Shook

[57] ABSTRACT

The centricular catheter 10 of the present invention comprises a multiplicity of inlet microtubules 12. Each microtubule has both a large opening 16 at its inlet end and a multiplicity of microscopic openings 18 along its lateral surfaces.

The microtubules are perforated by a new and novel ion beam sputter etch technique. The holes are etched in each microtubule by directing an ion beam 20 through an electro formed metal mesh mask 28 producing perforations having diameters ranging from about 14 microns to about 150 microns.

This combination of a multiplicity of fluoropolymer microtubes, the numerous small holes provided in the lateral surfaces of the tubes, and the hydra-like distribution of the tubes provide a new and novel catheter. This structure assures a reliable means for shunting cerebrospinal fluid from the cerebral ventricles to selected areas of the body.

17 Claims, 6 Drawing Figures

METHOD OF MAKING AN ION BEAM SPUTTER-ETCHED VENTRICULAR CATHETER FOR HYDROCEPHALUS SHUNT

ORIGIN OF THE INVENTION

The invention described herein was made by an employee of the United States Government and may be manufactured and used by or for the Government for governmental purposes without the payment of any royalties thereon or therefor.

RELATED APPLICATION

This application is a division of application of Ser. No. 272,407 which was filed June 10, 1981, and now U.S. Pat. No. 4,377,169 issued Mar. 22, 1983.

TECHNICAL FIELD

This invention is directed to an improved cerebrospinal fluid shunt in the form of a ventricular catheter for controlling the condition of hydrocephalus by relieving the excessive cerebrospinal fluid pressure. The invention is further concerned with an improved method for fabricating the catheter and an improved method of shunting the cerebral fluid from the cerebral ventricles to other areas of the body.

The obstruction of cerebrospinal fluid flow pathways or its inadequate absorption via the arachnoid villi into the venus blood of the brain results in hydrocephalus. Surgical correction involves pressure controlled shunting of the cerebrospinal fluid. Typically, a perforated silicon rubber catheter is implanted in one of the lateral ventricles of the brain with its perforated tip located near the frontal horn. The cerebrospinal fluid passes through a pressure regulating valve and is then typically shunted to the right atrium of the heart or the peritoneal cavity.

The shunt will fail to function if the inlet ventricular catheter apertures become blocked. Shunt flow failure will also occur if the ventricle collapses due to improper valve function causing over drainage.

Heretofore, previously designed ventricular catheters have been found deficient as a result of high incidence of inlet blockage caused by the ingrowth of the choroid plexas, ventrical collapse over the catheter orifices, or hemorrage, cellular, and fibrin debris. Multiple surgical revisions during the first several years after birth is common because of inlet blockage of the catheters.

Various geometry ventricular catheters have been proposed in which the inlet orifices are hidden or covered by complicated structures. The hidden inlet type geometries have not resulted in a decreased probability of blockage.

PRIOR ART

In the prior art U.S. Pat. No. 4,182,343 discloses a double ventricular drain tube having a double cavity. A rubber outer tube has one end which is sealed with the other end being open. This outer tube encloses a rubber inner tube that is shorter than the outer tube. One end of the inner tube is fixed to the inner wall of the sealed end of the outer tube and the other end of the inner tube is open. This inner tube may or may not be fixed to the inner wall of the outer tube. The outer tube and the inner tube, respectively, have a plurality of holes passing through their respective side walls. The holes through the outer tube side wall are positioned in such a manner so that they do not align with the holes in the side wall of the inner tube.

U.S. Pat. No. 3,595,241 discloses a medicosurgical tube having a swab member positioned inside the tube so constructed or arranged that it may be pulled through the tube and out the proximal end. In such a catheter, the lumen is positively protected throughout the tube length against the possibility of blood clots or other matter preventing liquid flow through the tube following the tube insertion procedure.

U.S. Pat. Nos. 3,753,439 and 3,823,782 disclose several types of surgical drains. These drains rely on relatively large holes in the tube wall, and a padding or net is utilized to prevent entry of material into the holes. None of the prior art patents discloses a catheter which would be suitable for insertion into the human brain.

DISCLOSURE OF THE INVENTION

The ventricular catheter of the present invention comprises a multiplicity of inlet microtubules. Each microtubule has both a large opening at its inlet end and a multiplicity of microscopic openings along its lateral surfaces.

The microtubules are perforated by a new and novel ion beam sputter etch technique. The holes are etched in each microtubule by directing an ion beam through an electro formed metal mesh mask producing perforations having diameters ranging from about 14 microns to about 150 microns.

This combination of a multiplicity of fluoropolymer microtubes, the numerous small holes provided in the lateral surfaces of the tubes, and the hydra-like distribution of the tubes provide a new and novel catheter. This structure assures a reliable means for shunting cerebrospinal fluid from the cerebral ventricles to selected areas of the body.

BRIEF DESCRIPTION OF THE DRAWINGS

The objects, advantages and novel features of the invention will be more fully apparent from the following detailed description when read in connection with the accompanying drawings wherein.

BEST MODE FOR CARRYING OUT THE INVENTION

Figure 1:
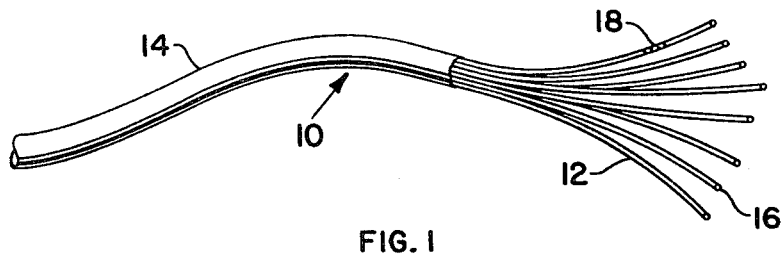
FIG. 1 is an enlarged view of a ventricular catheter constructed in accordance with the present invention.

Referring now to the drawing there is shown in FIG. 1 a ventricular catheter 10 constructed in accordance with the present invention. Each catheter 10 comprises a plurality of pliable microtubules 12. A bundle of the microtubules 12 may be covered by a tubular sheath 14 which is connected to a conventional valved shunting system.

The microtubules 12 are of a fluoropolymer material and can be varied in number, diameter, wall thickness, length and material. Typical fluoropolymers that are satisfactory for the microtubules 12 are polytetrafluoroethylene and fluoroethylene propylene. Living cells of the human body tend not to adhere to such materials, and no major anchorage problem results.

Figure 4:
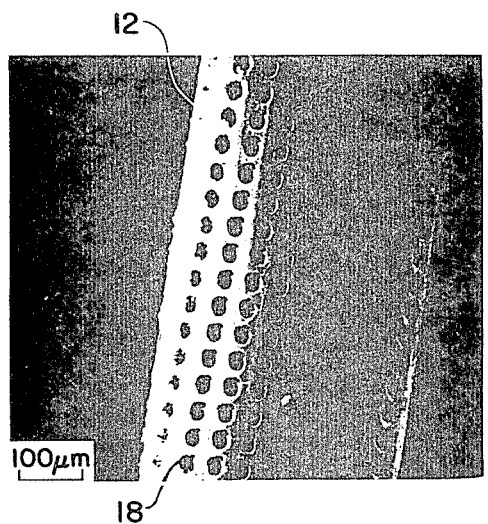
FIG. 4 is a scanning electron photomicrograph showing the outside surface of a sputter perforated microtubule.
Figure 5:
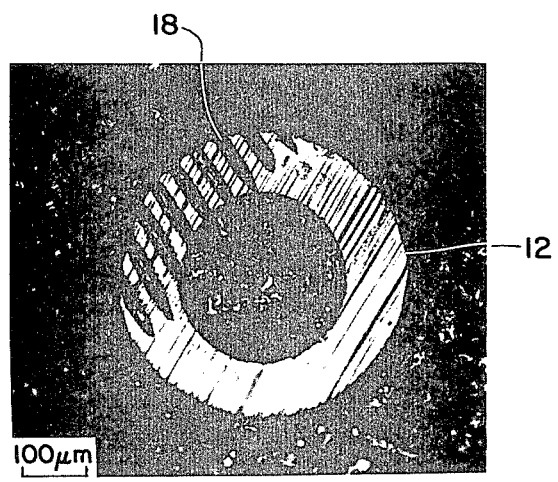
FIG. 5 is a scanning electron photomicrograph showing a sputter perforated microtubule in section.

Each microtubule 12 has an inlet end 16 which is preferably open and is of a larger diameter than each of the multiplicity of ion beam sputtered microscopic perforations 18 along a relatively long extent of the lateral surfaces as shown in greater detail in FIGS. 4 and 5. It is further contemplated that the inlet end 16 may be closed in certain embodiments.

The tubular sheath 14 is preferably of a silicone rubber tubing of small diameter to minimize the penetration thereby reducing the danger of infection. Silicon tubing having an outer diameter of about 0.015 m has been satisfactory. The type of transition from the fluorocarbon bundle to the silicone rubber tubing can be varied in geometry.

Figure 2:
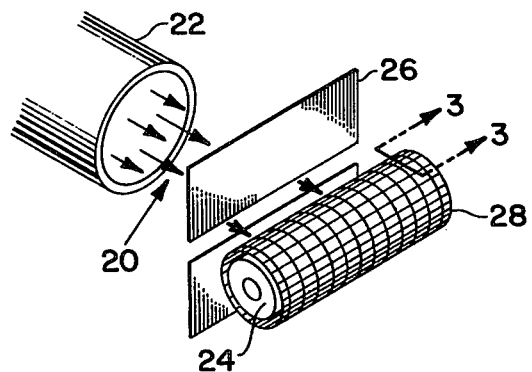
FIG. 2 is a schematic view showing apparatus for perforating the walls of the microtubules utilized in the catheter shown in FIG. 1.

Preselected areas of the microtubules 12 are perforated by exposing them to an ion beam 20 from a suitable source 22 as shown in FIG. 2. The ion beam 20 is between 300 eV and 500 eV with a density sufficient to perforate the microtubules 12 at a predetermined exposure time as shown in FIGS. 4 and 5.

The argon ion beam may be from an electron bombardment ion source 22 of the type developed from electric propulsion technology. Such an ion source is described in "Advances in Electronics and Electron Physics" by H. R. Kaufman, Vol. 36, pages 365 to 373.

Beam extraction may be accomplished by a dished, two grid ion optics system. Such a system is described in AIAA Paper No. 76-1017 entitled "A 30 cm Diameter ARgon Ion Source". Neutralization of the ion beam may be achieved by secondary electrons released by ion bombardment of the walls of a vacuum facility (not shown) which houses the ion source 22. This vacuum facility is sufficiently large to minimize back sputtered facility material from contaminating the material being ion beam etched. The vacuum facility normally is maintained at a pessure of $4 \times 10^{-5}$ torr during the operation of the ion source 22.

Microtubules 12 are mounted around the outer peripheral surface of a cylindrical mandrel 24 mounted for rotation about its normal axis downstream from the ion source 22. A suiable shield 26 is positioned between the source 22 and the mandrel 24 in close proximity with the mandrel. The ion beam 20 passes through the shield 26 in a manner well known in the art.

Figure 3:
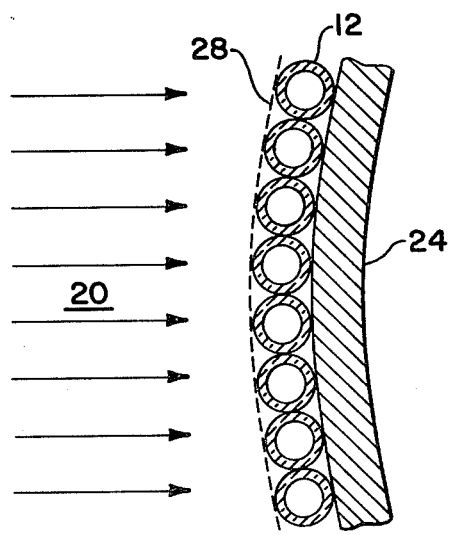
FIG. 3 is an enlarged sectional view taken along the lines 3—3 in FIG. 2.

An electroformed screen 28 of extremely fine mesh is held in tension around the outermost surface edges of the microtubules 12 on the mandrel 24 as shown in FIG. 3. Argon ions from the beam 20 pass through the screen 28 to form a pattern of perforations 18 as shown in FIG. 4. More particularly, the electroformed metal mesh screen 28 functions as a mask to produce the desired apertures through the walls in the microtubules 12. These apertures 18 are microscopic in size, having a diameter between about 20 $\mu$m and 150 $\mu$m. The portion of the ion beam 20 passing through the shield 26 is shown in FIG. 3 and is substantially uniform in density throughout its entire width.

The utilization of sputter etching to perforate the inlet ventricular catheter microtubules 12 facilitates the fabrication of catheters having two orders of magnitude increase in aperture density over that of conventional catheters shown in the prior art. This is evident because approximately 1100 apertures, each 20 $\mu$m in diameter, can be placed along a 1 cm length of microtubule.

The catheter 10 is comprised of a bundle of one or more microtubules 12, each being only about 0.44 mm in diameter. The resulting large number of inlet apertures reduces the tendency for the shunt to draw in and trap debris or tissue which would then cause flow obstruction.

Figure 6:
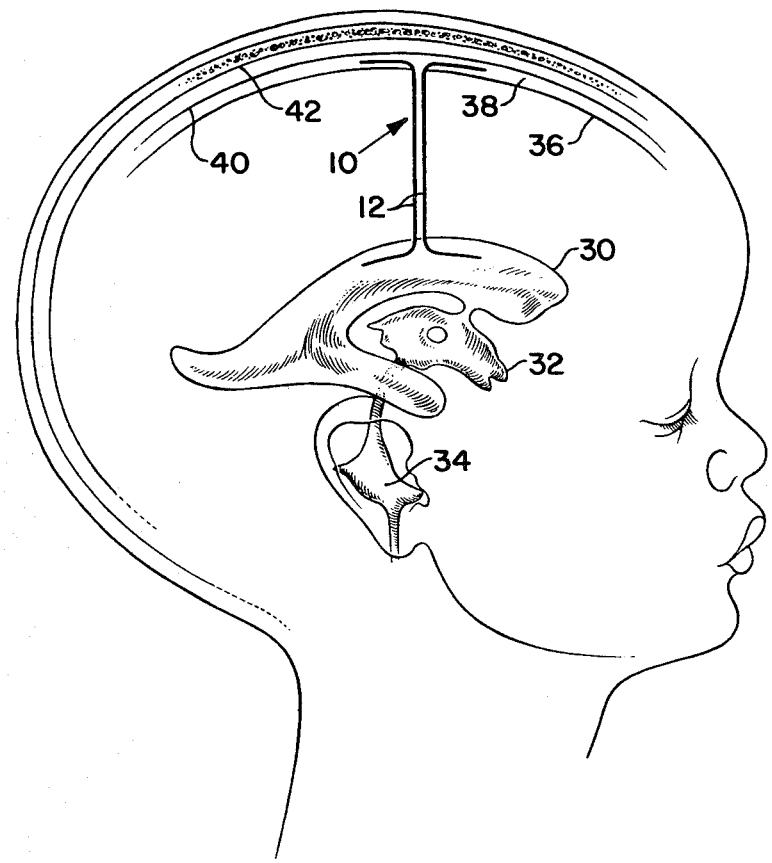
FIG. 6 is a schematic view showing the direct shunting of cerebrospinal fluid from a lateral ventricle to the subarachnoid space using sputter perforated microtubules.

The catheter 10 can be used to drain cerebrospinal fluid from one of the lateral ventricles through a conventional valved shunting system to either the heart or the peritonal cavity. The catheter also can be used for direct shunting of cerebrospinal fluid from a lateral ventricle 30 to selected areas of the human body using individual microtubules 12 as shown in FIG. 6. This lateral ventricle 30 is in substantial justaposition with the third ventricle 32 which is positioned above the fourth ventricle 34.

The microtubules 12 extend from the lateral ventricle up through the pia mater to the subarachnoid space 38. This space is between the pia mater 36 and the arachnoid 40 which is positioned inwardly from the dura mater 42. The inlet ends 16 of the microtubules 12 extend into the lateral ventricle 30 in a hydra-like fashion. Likewise, the outermost or discharge end of the microtubules 12 extend hydra-like in the subarachnoid space 38.

It will be appreciated the positioning of the catheter 10 as shown in FIG. 6 does not require any pressure regulating valves. Such valves are used with conventional catheters that return the cerebrospinal fluid to the heart or peritonal cavity. Also, this procedure returns the cerebrospinal fluid to its site of normal absorption in the subarachnoid space 38.

The large number of inlet apertures 18 formed by the perforations reduces the tendency for a shunt to draw in and trap debris or tissue which would then flow or cause flow obstruction. Also, this combination of extremely small apertures in the lateral surfaces of the microtubules together with the fluoropolymer material of the microtubules reduces the mechanical attachment of tissue and aids revisions if needed. The small diameter of the perforations 18 reduces the probability of cerebrospinal fluid flow blockage caused by localized collapse of the ventricle.

While the preferred embodiment of the invention has been described it will be appreciated that various structural modifications and procedural changes may be made without departing from the spirit of the invention or the scope of the subjoined claims. More particularly, it is contemplated that both the material and the geometry of the sputter mask mesh 28 can be varied. This, in turn, changes the positioning as well as the configuration of the perforations 18 in the microtubules 12. It is also contemplated that while the microtubules 12 are shown mounted on a mandrel 24 in a substantially parallel juxtaposition, as shown in both FIGS. 2 and 3, other mounting arrangements may be relied on. More particularly, the microtubules 12 may be wrapped on the mandrel 24 in a spiral mounting. It is further contemplated that the microtubules 12 shown in FIG. 3 may be twisted and held in a twisted position during ion sputtering. Subsequent to the perforations 18 being formed the twisting forces are removed so that the perforations then have a general spiral configuration about the walls of the microtubules 12.

I claim:

1. In a method of making a ventricular catheter for controlling the condition of hydrocephalus by relieving the excessive cerebrospinal fluid pressure comprising the steps of covering at least one end portion of each of a plurality of microtubular members with a mask having a plurality of microscopic openings therein, placing said covered microtubular members in a vacuum environment, and exposing said mask to a beam of ions whereby perforations are produced in said end portions of said microtubular members.

2. A method of making a ventricular catheter as claimed in claim 1 wherein the microtububular members are of a fluoropolymer material.

3. A method of making a ventricular catheter as claimed in claim 2 wherein the microtubular members are of a fluoropolymer material selected from the group consisting of polytetrafluoroethylene, and fluoroethylene propylene.

4. A method of making a ventricular catheter as claimed in claim 2 wherein the microtubular members have diameters of about 0.44 mm.

5. A method of making a ventricular catheter as claimed in claim 4 wherein the perforations in the microtubular members have diameters between about 14 microns and 150 microns.

6. A method of making a ventricular catheter as claimed in claim 1 including the step of enclosing a plurality of said perforated microtubular members in a tubular sheath.

7. A method of making a ventricular catheter as claimed in claim 6 wherein the tubular sheath is of a silicone rubber material.

8. A method of making a ventricular catheter as claimed in claim 6 wherein said perforated portions of said microtubular members extend from an end of said sheath.

9. A method of making a ventricular catheter as claimed in claim 6 wherein the tubular sheath has a diameter of about 0.015 m.

10. A method of making a ventricular catheter as claimed in claim 1 wherein the mask is electroformed metal mesh having openings with diameters between about 20 $\mu$m and about 150 $\mu$m.

11. A method of making a ventricular catheter as claimed in claim 1 including the steps of mounting the microtubular members on a cylindrical supporting means located downstream from a source of ions, positioning the mask between said ion source and said supporting means in close proximity with said supporting means, and rotating said supporting means about its normal axis.

12. A method of making a ventricular catheter as claimed in claim 11 wherein the supporting means is mounted in a vacuum environment having a pressure of about $4 \times 10^{-5}$ torr.

13. A method of making a ventricular catheter as claimed in claim 12 wherein the masked portions of the microtubular members on the supporting means are exposed to a beam of argon ions.

14. A method of making a ventricular catheter as claimed in claim 13 wherein the beam of argon ions is between 300 eV and 500 eV.

15. A method of making a ventricular catheter as claimed in claim 11 wherein the microtubular members are mounted around the outer peripheral surface of a cylindrical mandrel member in a substantially parallel juxtaposition.

16. A method of making a ventricular catheter as claimed in claim 11 wherein the microtubular members are wrapped around the outer peripheral surface of a cylindrical mandrel member in a spiral configuration.

17. A method of making a ventricular catheter as claimed in claim 11 including the steps of applying a twisting force to the microtubular member, maintaining said twisting force on said microtubular members during ion sputtering, and removing said twisting force subsequent to forming the perforations whereby said perforations have a general spiral configuration about the walls of said microtubular members.

* * * * *